United States Patent [19]
Rossignol et al.

[11] Patent Number: 5,158,497
[45] Date of Patent: Oct. 27, 1992

[54] MATING CHAMBER FOR HONEY BEES

[75] Inventors: Philippe A. Rossignol; Lynn A. Royce, both of Corvallis; Beryl A. Stringer, Blodgett, all of Oreg.

[73] Assignee: The State of Oregon Acting by and Through the Oregon State Board of Higher Education on Behalf of Oregon State University, Corvallis, Oreg.

[21] Appl. No.: 652,177

[22] Filed: Feb. 7, 1991

[51] Int. Cl.[5] ............................................. A01K 47/00
[52] U.S. Cl. ........................................ 449/2; 449/3; 119/6.5
[58] Field of Search .............. 449/2, 3, 8, 28, 50; 119/6.5, 15

[56] References Cited

U.S. PATENT DOCUMENTS

| 948,805 | 2/1910 | Akerlind | 119/6.5 |
| 3,814,057 | 6/1974 | Calvert et al. | 119/15 |
| 4,250,833 | 2/1981 | Waldon | 119/6.5 |

FOREIGN PATENT DOCUMENTS 2328475  1/1975  Fed. Rep. of Germany ......... 449/8

Primary Examiner—Robert P. Swiatek
Attorney, Agent, or Firm—Klarquist, Sparkman, Campbell, Leigh & Whinston

[57] ABSTRACT

An enclosure for the controlled breeding of honey bees has a diffusely illuminated upper dome section. The dome is illuminated either by upwardly directed light reflected or emitted from a lower portion of the enclosure, or by an external source diffused through the dome. A queen bee is tethered in the center of the enclosure below the dome.

23 Claims, 1 Drawing Sheet

MATING CHAMBER FOR HONEY BEES

TECHNICAL FIELD

This invention relates to an apparatus for breeding honey bees, and more particularly to an apparatus which encloses and isolates the bees to be bred.

BACKGROUND ART

Honey bees normally breed in nature without the aid of any apparatus. The female or queen bee is normally inseminated by a number of male or drone bees while the queen and the males are in flight. This process is known as "open mating." Open mating, however, does not permit human control over the mating process, making selective breeding nearly impossible. More importantly, a free-flying queen is susceptible to fertilization by undesirable Africanized bees which pass on their dangerous and non-productive traits to the queen's offspring.

Currently, controlled breeding is achieved by instrumental insemination with semen yielded by the desired male breeding stock. Instrumental insemination is insufficient for production colonies, and is time consuming. The process requires precision instruments and highly skilled operators. In addition, those queen bees fertilized by instrumental insemination generally produce substantially less offspring, with this reduction in fecundity further reducing the breeding efficiency.

Previous attempts at achieving free mating of bees in an enclosed chamber have been unsuccessful. The use of a point source of light to illuminate the chamber attracts the bees to the light and away from a queen bee. Also, previous chambers have been too large for effective free mating. A further disadvantage of previous chambers is that visible landmarks, such as the corners of a box-shaped enclosure, distract the drone bees from the mating process. In addition previous attempts at enclosed free mating have used a free flying queen bee. Because queen bees cannot effectively hover like drones, the queen flies through the chamber until it hits one of the walls. This can result in injury to the queen and reduces the likelihood of successful free mating.

SUMMARY OF THE INVENTION

It is an object of the present invention to provide an apparatus for the controlled breeding of honey bees.

A further object of the invention is to prevent the breeding bees from being intruded upon by genetically undesirable bees.

It is yet another object of the invention to provide a breeding apparatus which requires minimal operator skill.

It is yet another object of the invention to provide a breeding apparatus which provides a high yield of desired offspring from the breeding process.

The invention achieves these and other objects by providing an enclosure for containing the breeding stock. The enclosure has a diffusely illuminated upper dome portion and a tethering device for restraining the queen bee at a central position beneath the dome whereby the male drones can effectively inseminate the queen while the drones are in flight.

DETAILED DESCRIPTION OF A PREFERRED EMBODIMENT

Figure 1:
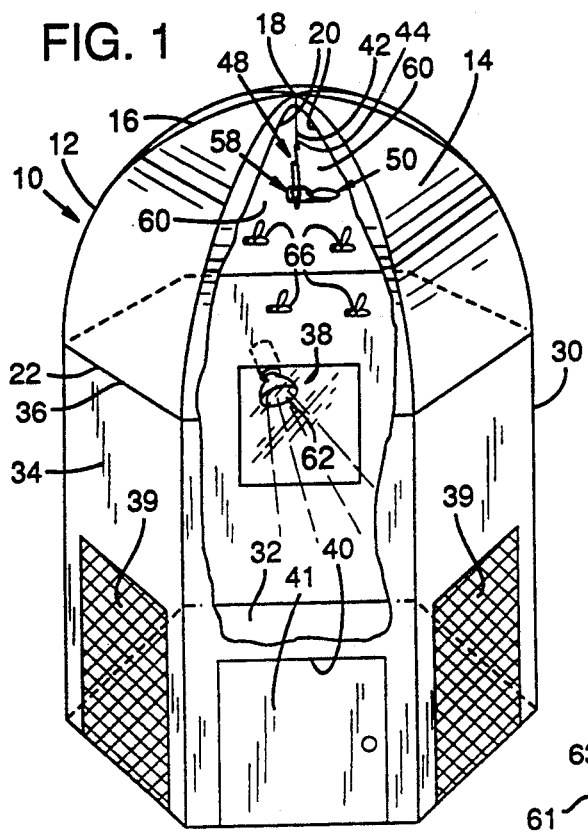
FIG. 1 is a cut-away perspective view of an apparatus constructed in accordance with the invention.

Referring to the drawings, FIG. 1 illustrates a honey bee breeding enclosure 10 constructed in accordance with the invention with portions removed for illustrative clarity. An upper dome portion 12 forms the top of the enclosure. The dome has a plurality of facets 14, each facet being curved about a horizontal axis and joined to adjacent facets at facet seams 16 at obtuse angles preferably not less than 120 degrees. The facet seams intersect at the apex 18 of the dome and radiate outwardly therefrom. Each facet has three edges. The first and second edges being curved radial edges 20 meeting at the apex, the third edge being the perimeter edge 22, the perimeter edge being horizontal and forming a portion of the lower edge of the dome. The dome is generally in the form of a downwardly concave hemisphere with the facets forming gore-like panels. The dome may be provided with screened observation or access apertures (not shown).

A lower portion 30 of the enclosure is generally cylindrical and has a rigid bottom panel 32 having a reflective upper surface and rigid vertical side walls 34, the side walls having upper edges 36 in a horizontal plane, each side wall upper edge corresponding to and sealed to a perimeter edge 22 of a facet 14 of the dome 12. In a preferred embodiment, all panels of the enclosure are preferably formed of an opaque sheet material such as aluminum or steel, the panels being folded from unitary sheets or bolted together by suitable means.

One of the vertical side walls 34 defines a light port 38 which passes light therethrough while providing a barrier to bees. The port is preferably a screened panel and may alternatively be a transparent glass or plastic sheet. The light port is positioned at an intermediate height, nearer the upper edge 36 of the side wall. Vents 39 are provided in the lower portions of at least two of the side walls proximate to the bottom panel 32. The vents permit the flow of air therethrough and prevent the escape of bees. The vents also may be provided with optional fans and temperature control apparatus (not shown). An access port 40 is provided in a lower portion of a sidewall proximate to the bottom panel. The access port has a removable door 41 sized to close the port to prevent the escape of the bees. The access port is sized to permit an operator to introduce drones into the enclosure. An adjustable elongated member 42 extends perpendicularly downward from the apex 18 of the dome towards the center of the enclosure. The adjustable elongated member terminates at a distal end 44 located generally vertically below the apex 18 of the dome 12 and generally above the plane of the perimeter edge 22 of the dome. The elongated member is preferably a flexible thread which may be adjusted to vary the height of distal end. The distal end may be formed by a segment of wire attached to the thread of the elongated member.

Figure 2:
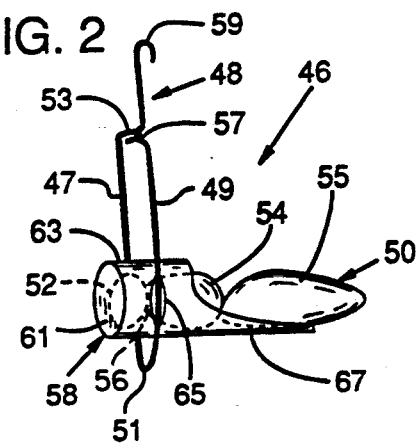
FIG. 2 is an enlarged perspective view of a tethering device of the apparatus of FIG. 1.
Figure 3:
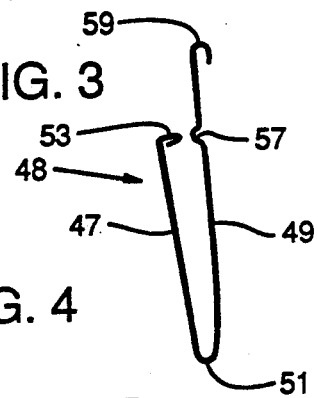
FIG. 3 is an enlarged plan view of the harness of the tethering device of FIG. 2.

As best shown in FIG. 2, a tethering device 46 is attached to the distal end of the elongated member. The tethering device comprises a pin or harness 48 sized and shaped to removably and selectably secure a queen bee 50 having a head 52, a thorax 54 and an abdomen 55, the harness being sized to engage the narrowed neck region 56 between the head and the thorax. Alternatively, the collar may engage a narrowed waist region between the thorax 54 and the abdomen 55. The collar is formed by a spring wire, as shown in FIG. 3, having a first vertical side 47 and a second vertical side 49 joined at a lower bend 51. The sides are separated by a gap sufficient to retain the queen without injury, preferably about 2 to 3 millimeters. The first side has an upward distal end 53 terminated in a hook sized to engage the second side at a detent 57 in the manner of a traditional safety pin. The second side is upwardly terminated by a hook end 59 which engages the elongated member 42. Alternatively, the tethering device may include a flexible thread segment (not shown) having a first end attached to the distal end 44 of the elongated member 42, and the thread segment having a second end attached to the hook end of the harness.

Figure 4:
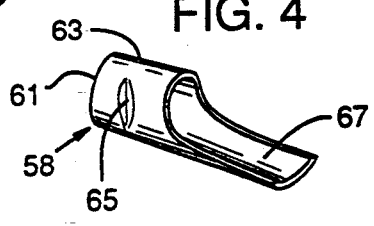
FIG. 4 is an enlarged perspective view of the hood of the tethering device of FIG. 2.
Figure 5A:
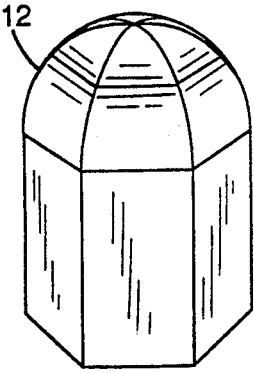
FIGS. 5a-5d are perspective views of alternate dome configurations constructed in accordance with the invention.
Figure 5B:
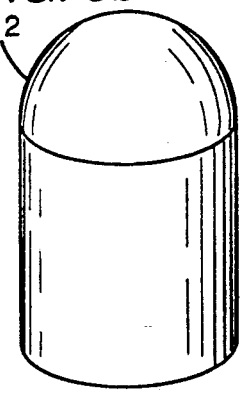
Figure 5C:
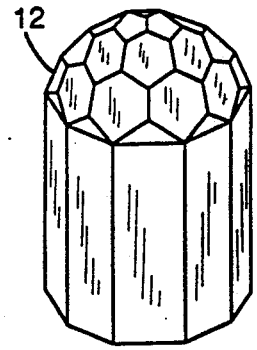
Figure 5D:
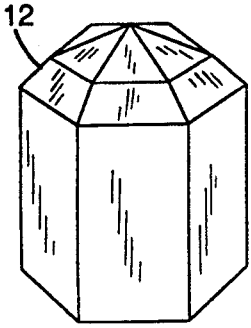

The tethered queen bee 50 is provided with a cylindrical hood 58 as shown in FIG. 4 with the bee's head and thorax inserted therein. The hood is preferably formed of a translucent plastic material to permit passage of ambient light while preventing the queen bee's perception of visual distractions. The hood is of a sufficient diameter to receive the queen 50, preferably about 6 mm. The hood has a closed end wall 61 corresponding to the head of the queen. The hood has a cylindrical wall 63 extending from the closed end wall about 5 mm. Vertical harness slots 65 are defined at intermediate positions on opposite sides of the cylindrical wall, and are sized to receive the harness about the neck 56 of the queen. Extending from a lower portion of the cylindrical wall opposite the end wall is an elongated shelf 67 which supports the abdomen of the queen as shown in FIG. 2. The shelf is preferably about 5 mm in length. As an alternative to the hood, the eyes of the queen may be painted with a translucent material to prevent unwanted distractions.

The tethering device may, in the alternative, comprise a plurality of spaced-apart harnesses suspended from the elongated member 42 on a rigid wire hanger apparatus (not shown).

The dome 12 has a downwardly facing interior surface 60 which is illuminated by illumination means provided by an exterior source of light such as the sun or artificial light which shines through the light port 38 and illuminates the reflective upper surface of the bottom panel 32, wherefrom the light is upwardly reflected toward the interior surface 60 of the dome. The bottom panel reflective surface is preferably provided by a matte white paint finish.

In an alternative embodiment, the illumination means is provided by an upwardly directed light source positioned to provide the interior surface 60 of the dome 12 with generally even illumination. Such a light source, which may be located in the lower portion of the enclosure 30, preferably includes a plurality of upwardly directed light bulbs.

The illuminated interior surface 60 of the dome 12 is preferably a lambertian surface, whereby each point on the surface reflects light at an equal intensity in all directions. Such a surface may be achieved by painting the interior surface with a matte white paint finish. Alternatively, a lambertian surface may be achieved by texturing methods such as sandblasting.

In another alternative embodiment, the dome 12 may be fabricated of a translucent material with the illumination means shining light on the exterior surface of the dome 12 whereby it is diffused through the dome causing the interior surface 60 to appear illuminated.

In yet another alternative embodiment, the dome 12 may be transparent, with a diffuse light source being provided in the hemispheric region above the dome, such as by a second external dome with an illuminated interior surface.

Operation

The bee breeding chamber is employed by attaching a queen bee 50 to the collar 48 on the tethering device 46 and inserting it into the enclosure 10 while sealing the access aperture 40. Drone bees are thereafter introduced into the enclosure. The temperature in the enclosure is preferably maintained at 82° F. and does not vary by more than 10° F. from the preferred temperature. Ventilation is provided by vents 39 and a fan (not shown). Humidity in the chamber is preferably maintained at between 35% and 55% relative humidity. The illumination means 62 should be constructed to provide light which simulates natural sunlight. Suitable light can be provided by high cycle fluorescent lights, preferably 40 w fluorescent bulbs having high ultraviolet intensity with staggered flicker cycles resulting in a net 360 cycles per second preferred flicker rate. The flicker rate is at least 300 cycles per second.

In the foregoing it will be apparent that the described breeding enclosure is capable of providing a controlled environment for the breeding of honey bees. It has the advantages of simple operation and effective fertilization of the queen bee while avoiding the intrusion of unwanted breeding stock. Moreover, the enclosure may be simply and easily constructed of ordinary materials and might appropriately be employed even by small farmers.

Having illustrated and described the principles of our invention by what is presently a preferred embodiment, it should be apparent to those persons skilled in the art that the illustrated embodiment may be modified without departing from such principles. We claim as our invention not only the illustrated embodiment but all such modifications, variations, and equivalents thereof as come within the true spirit and scope of the following claims.

We claim:

1. Apparatus for the controlled mating of flying insects of the type which copulate while in flight, the apparatus comprising:
    a lower portion; and
    an illuminated dome attached to the lower portion to define therewith an enclosure for containing the insects,
wherein the dome scatters incident light to present a generally diffuse evenly illuminated appearance, without a point source of light that attracts insects when viewed from within the enclosure.

2. The apparatus of claim 1 wherein the dome comprises a plurality of facets, each facet forming an obtuse angle with each adjacent facet.

3. The apparatus of claim 2 wherein at least some of the facets are curved.

4. The apparatus of claim 2 wherein the angle between any two adjacent facets is not less than 120 degrees.

5. The apparatus of claim 1 wherein the dome is illuminated from the exterior thereof.

6. The apparatus of claim 5 wherein the dome is translucent and the light source is positioned outside of the enclosure for illuminating the dome.

7. The apparatus of claim 1 wherein the dome is illuminated from below.

8. The apparatus of claim 1 also having a bottom panel below the dome and a transparent light port, wherein the source of light is a beam of light directed into the enclosure through the light port onto the bottom panel, wherefrom it is upwardly reflected.

9. An apparatus for the controlled mating of flying insects of the type which copulate while in flight, the apparatus comprising:
   a lower portion;
   an illuminated dome attached to the lower portion to define therewith an enclosure for containing insects; and
   a tethering device for holding an insect carrying eggs to be fertilized within the enclosure at a generally central point beneath the dome.

10. The apparatus of claim 9 wherein the tethering device comprises a harness sized to retain an insect at a narrowed region of the insect's body.

11. The apparatus of claim 9 wherein the tethering device includes a hood for covering the eyes of the insect.

12. The apparatus of claim 11 wherein the hood is translucent.

13. The apparatus of claim 11 wherein the hood is a cylindrical tube which is open at one end.

14. A method of mating flying insects of the type which copulate while in flight, the method comprising:
   enclosing insects to be mated within a chamber partially defined by a light scattering dome; and
   diffusely illuminating the dome interior surface in such a manner that insects in flight inside the chamber cannot see an exterior point source of light when viewing the dome.

15. The method of claim 14 wherein the insects are honey bees.

16. A method of mating flying insects of the type which copulate while in flight, the method comprising:
   enclosing insects to be mated within a chamber partially defined by an illuminated dome; and
   tethering within the chamber a female insect to be fertilized, the female insect being tethered in such a manner that the female insect can be fertilized by a male insect while the male insect is in flight.

17. The method of claim 16 wherein the tethered insect is secured at a region between its head and thorax.

18. The method of claim 16 wherein the tethered insect is secured at a region between its thorax and abdomen.

19. The method of claim 16 wherein the tethered insect is tethered generally centrally within the dome.

20. The method of claim 16 wherein the tethered insect is tethered at generally above the lowest portion of the dome.

21. The method of claim 16 wherein the head of the tethered insect is placed within a translucent tube.

22. The method of claim 16 including the step of painting the tethered insect's eyes with translucent paint.

23. An enclosure for the controlled breeding of honey bees comprising:
   an upper dome portion having a diffusely reflective interior surface and having a lower perimeter in a generally horizontal plane;
   a lower portion having an upper perimeter sealed to the lower perimeter of the dome whereby a space is enclosed from which insects cannot escape;
   a light source for evenly illuminating the interior surface of the dome;
   a tethering device having a harness sized to capture and restrain a narrowed region of a queen bee to be fertilized, the harness collar being positioned generally centrally within the enclosure at a height generally above the lower perimeter of the dome.

* * * * *